(12) United States Patent
Pidgeon et al.

(10) Patent No.: US 8,294,586 B2
(45) Date of Patent: Oct. 23, 2012

(54) TOPICAL NEGATIVE PRESSURE SYSTEM WITH STATUS INDICATION

(76) Inventors: Andrew Duncan Pidgeon, Whittlesford (GB); Richard Mann, Cambridge (GB); Max William Middleton, London (GB)

( * ) Notice: Subject to any disclaimer, the term of this patent is extended or adjusted under 35 U.S.C. 154(b) by 338 days.

(21) Appl. No.: 12/667,229

(22) PCT Filed: Jun. 20, 2008

(86) PCT No.: PCT/GB2008/002113
§ 371 (c)(1),
(2), (4) Date: Dec. 29, 2009

(87) PCT Pub. No.: WO2009/004289
PCT Pub. Date: Jan. 8, 2009

(65) Prior Publication Data
US 2010/0207768 A1    Aug. 19, 2010

(30) Foreign Application Priority Data
Jul. 2, 2007   (GB) .................................. 0712760.8

(51) Int. Cl.
G08B 23/00      (2006.01)
A61B 5/05       (2006.01)
A61F 13/00      (2006.01)
A61M 1/00       (2006.01)

(52) U.S. Cl. .................... 340/573.1; 600/407; 604/319; 604/305; 604/313

(58) Field of Classification Search .................. None
See application file for complete search history.

(56) References Cited

U.S. PATENT DOCUMENTS

| 5,760,754 | A | 6/1998 | Amero, Jr. et al. |
| 5,988,842 | A | 11/1999 | Johnsen et al. |
| 6,129,440 | A | 10/2000 | Reynolds |
| 6,402,702 | B1 * | 6/2002 | Gilcher et al. ............... 600/573 |
| 6,692,132 | B1 | 2/2004 | Meeker |
| 7,214,202 | B1 | 5/2007 | Vogel et al. |
| 2002/0198504 | A1 * | 12/2002 | Risk et al. .................... 604/318 |
| 2003/0097100 | A1 | 5/2003 | Watson |
| 2007/0032762 | A1 * | 2/2007 | Vogel ............................ 604/305 |
| 2007/0055209 | A1 * | 3/2007 | Patel et al. .................... 604/315 |
| 2007/0066946 | A1 * | 3/2007 | Haggstrom et al. .......... 604/313 |

(Continued)

FOREIGN PATENT DOCUMENTS

GB    2307180    5/1997

(Continued)

OTHER PUBLICATIONS

International Search Report from PCT/GB2008/002113 mailed Jan. 22, 2009 in 8 pages.

(Continued)

*Primary Examiner* — Daniel Wu
*Assistant Examiner* — Emily C Terrell
(74) *Attorney, Agent, or Firm* — Knobbe Martens Olson & Bear LLP

(57) ABSTRACT

A method and apparatus are disclosed for indicating a status of at least one operating parameter associated with a topical negative pressure (TNP) system. The method includes the steps of generating illumination from at least one LED, the illumination having at least one characteristic corresponding to a status of at least one operating parameter associated with the TNP system and being visible to a user.

18 Claims, 9 Drawing Sheets

U.S. PATENT DOCUMENTS

2007/0265586 A1  11/2007  Joshi et al.
2008/0071216 A1  3/2008  Locke et al.

FOREIGN PATENT DOCUMENTS

| | | |
|---|---|---|
| GB | 2342584 | 4/2000 |
| WO | WO 00/17968 | 3/2000 |
| WO | WO 00/61206 | 10/2000 |
| WO | WO 03/101508 | 12/2003 |
| WO | WO 2007/019038 | 2/2007 |
| WO | WO 2007/030598 | 3/2007 |
| WO | WO 2007/067685 | 6/2007 |
| WO | WO 2007/087808 | 8/2007 |
| WO | WO 2008/049029 | 4/2008 |

OTHER PUBLICATIONS

Info V.A.C. User Manual—KCI—Dec. 2006 (76 pages).
Written Opinion from PCT/GB2008/002113 mailed Jan. 22, 2009 in 7 pages.

* cited by examiner

TOPICAL NEGATIVE PRESSURE SYSTEM WITH STATUS INDICATION

CROSS-REFERENCE TO RELATED APPLICATIONS

This application is a U.S. National Phase of the PCT International Application No. PCT/GB2008/002113 filed on Jun. 20, 2008, designating the U.S. and published on Jan. 8, 2009 as WO 2009/00489, which claims priority to Great Britain Patent Application No. 0712760.8 filed on Jul. 2, 2007. The disclosure of both prior applications is incorporated by reference in their entirety and should be considered a part of this specification.

BACKGROUND OF THE INVENTION

Field of Invention

The present invention relates to apparatus and a method for the application of topical negative pressure (TNP) therapy to wounds. In particular, but not exclusively, the present invention relates to a method and apparatus for indicating one or more operating parameters of the TNP system.

Background of the Invention

There is much prior art available relating to the provision of apparatus and methods of use thereof for the application of TNP therapy to wounds together with other therapeutic processes intended to enhance the effects of the TNP therapy. Examples of such prior art include those listed and briefly described below.

TNP therapy assists in the closure and healing of wounds by reducing tissue oedema; encouraging blood flow and granulation of tissue; removing excess exudates and may reduce bacterial load and thus, infection to the wound. Furthermore, TNP therapy permits less outside disturbance of the wound and promotes more rapid healing.

In our co-pending International patent application, WO 2004/037334, apparatus, a wound dressing and a method for aspirating, irrigating and cleansing wounds are described. In very general terms, this invention describes the treatment of a wound by the application of topical negative pressure (TNP) therapy for aspirating the wound together with the further provision of additional fluid for irrigating and/or cleansing the wound, which fluid, comprising both wound exudates and irrigation fluid, is then drawn off by the aspiration means and circulated through means for separating the beneficial materials therein from deleterious materials. The materials which are beneficial to wound healing are recirculated through the wound dressing and those materials deleterious to wound healing are discarded to a waste collection bag or vessel.

In our co-pending International patent application, WO 2005/04670, apparatus, a wound dressing and a method for cleansing a wound using aspiration, irrigation and cleansing wounds are described. Again, in very general terms, the invention described in this document utilises similar apparatus to that in WO 2004/037334 with regard to the aspiration, irrigation and cleansing of the wound, however, it further includes the important additional step of providing heating means to control the temperature of that beneficial material being returned to the wound site/dressing so that it is at an optimum temperature, for example, to have the most efficacious therapeutic effect on the wound.

In our co-pending International patent application, WO 2005/105180, apparatus and a method for the aspiration, irrigation and/or cleansing of wounds are described. Again, in very general terms, this document describes similar apparatus to the two previously mentioned documents hereinabove but with the additional step of providing means for the supply and application of physiologically active agents to the wound site/dressing to promote wound healing.

The content of the above references is included herein by reference.

However, the above apparatus and methods are generally only applicable to a patient when hospitalised as the apparatus is complex, needing people having specialist knowledge in how to operate and maintain the apparatus, and also relatively heavy and bulky, not being adapted for easy mobility outside of a hospital environment by a patient, for example.

Some patients having relatively less severe wounds which do not require continuous hospitalisation, for example, but whom nevertheless would benefit from the prolonged application of TNP therapy, could be treated at home or at work subject to the availability of an easily portable and maintainable TNP therapy apparatus.

GB-A-2 307 180 describes a portable TNP therapy unit which may be carried by a patient clipped to belt or harness. It will be appreciated that a number of operating parameters such as power and operating efficiency may not be quickly and simply derivable to a user.

In many known portable units certain parameters associated with operation of the portable unit such as time remaining due to battery life, number of doses left, whether operation is running smoothly or whether there is a potential fault are not indicated to a user at all. This means that a user may be unaware of any potential problems and may be unable to take predictive action. Furthermore some portable units which provide some type of user display do so in a manner which is complicated and thus prone to reading error on the part of a user. Such displays may also utilise large quantities of power which can reduce available run/operation time.

A still further problem with known portable units is that displays used to display conditions of certain parameters may not be easy to see and/or read from a distance. This is particularly so for LCD displays and when there are low light conditions such as night time operation

SUMMARY OF SOME EXEMPLIFYING EMBODIMENTS

It is an aim of the present invention to at least partly mitigate the above-mentioned problems.

It is an aim of embodiments of the present invention to provide a method and apparatus for indicating the status of one or more parameters associated with the TNP system. It is an aim of further embodiments of the present invention to provide a manner of providing a user with status information in a manner which is readily available, easy to understand and thus not prone to error and yet which does not unduly drain a portable unit of power.

According to a first aspect of the present invention there is provided a method of indicating status of at least one operating parameter associated with a topical negative pressure (TNP) system, comprising the steps of:

generating a cue having at least one characteristic corresponding to a status of at least one operating parameter associated with the TNP system.

The invention is comprised in part of an overall apparatus for the provision of TNP therapy to a patient in almost any environment. The apparatus is lightweight, may be mains or battery powered by a rechargeable battery pack contained within a device (henceforth, the term "device" is used to connote a unit which may contain all of the control, power supply, power supply recharging, electronic indicator means and means for initiating and sustaining aspiration functions to a wound and any further necessary functions of a similar nature). When outside the home, for example, the apparatus may provide for an extended period of operation on battery power and in the home, for example, the device may be connected to the mains by a charger unit whilst still being used and operated by the patient.

The overall apparatus of which the present invention is a part comprises: a dressing covering the wound and sealing at least an open end of an aspiration conduit to a cavity formed over the wound by the dressing; an aspiration tube comprising at least one lumen therethrough leading from the wound dressing to a waste material canister for collecting and holding wound exudates/waste material prior to disposal; and, a power, control and aspiration initiating and sustaining device associated with the waste canister.

The dressing covering the wound may be any type of dressing normally employed with TNP therapy and, in very general terms, may comprise, for example, a semi-permeable, flexible, self-adhesive drape material, as is known in the dressings art, to cover the wound and seal with surrounding sound tissue to create a sealed cavity or void over the wound. There may aptly be a porous barrier and support member in the cavity between the wound bed and the covering material to enable an even vacuum distribution to be achieved over the area of the wound. The porous barrier and support member being, for example, a gauze, a foam an inflatable bag or known wound contact type material resistant to crushing under the levels of vacuum created and which permits transfer of wound exudates across the wound area to the aspiration conduit sealed to the flexible cover drape over the wound.

The aspiration conduit may be a plain flexible tube, for example, having a single lumen therethrough and made from a plastics material compatible with raw tissue, for example. However, the aspiration conduit may have a plurality of lumens therethrough to achieve specific objectives relating to the invention. A portion of the tube sited within the sealed cavity over the wound may have a structure to enable continued aspiration and evacuation of wound exudates without becoming constricted or blocked even at the higher levels of the negative pressure range envisaged.

It is envisaged that the negative pressure range for the apparatus embodying the present invention may be between about −50 mmHg and −200 mmHg (note that these pressures are relative to normal ambient atmospheric pressure thus, −200 mmHg would be about 560 mmHg in practical terms). Aptly, the pressure range may be between about −75 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg.

The aspiration conduit at its distal end remote from the dressing may be attached to the waste canister at an inlet port or connector. The device containing the means for initiating and sustaining aspiration of the wound/dressing may be situated between the dressing and waste canister, however, in a preferred embodiment of the apparatus embodying the present invention, the device may aspirate the wound/dressing via the canister thus, the waste canister may preferably be sited between the wound/dressing and device.

The aspiration conduit at the waste material canister end may preferably be bonded to the waste canister to prevent inadvertent detachment when being caught on an obstruction, for example.

The canister may be a plastics material moulding or a composite unit comprising a plurality of separate mouldings. The canister may aptly be translucent or transparent in order to visually determine the extent of filling with exudates. However, the canister and device may in some embodiments provide automatic warning of imminent canister full condition and may also provide means for cessation of aspiration when the canister reaches the full condition.

The canister may be provided with filters to prevent the exhaust of liquids and odours therefrom and also to prevent the expulsion of bacteria into the atmosphere. Such filters may comprise a plurality of filters in series. Examples of suitable filters may comprise hydrophobic filters of 0.2 μm pore size, for example, in respect of sealing the canister against bacteria expulsion and 1 μm against liquid expulsion.

Aptly, the filters may be sited at an upper portion of the waste canister in normal use, that is when the apparatus is being used or carried by a patient the filters are in an upper position and separated from the exudate liquid in the waste canister by gravity. Furthermore, such an orientation keeps the waste canister outlet or exhaust exit port remote from the exudate surface.

Aptly the waste canister may be filled with an absorbent gel such as ISOLYSEL (trade mark), for example, as an added safeguard against leakage of the canister when full and being changed and disposed of. Added advantages of a gel matrix within the exudate storing volume of the waste canister are that it prevents excessive movement, such as slopping, of the liquid, minimises bacterial growth and minimises odours.

The waste canister may also be provided with suitable means to prevent leakage thereof both when detached from the device unit and also when the aspiration conduit is detached from the wound site/dressing.

The canister may have suitable means to prevent emptying by a user (without tools or damage to the canister) such that a full or otherwise end-of-life canister may only be disposed of with waste fluid still contained.

The device and waste canister may have mutually complementary means for connecting a device unit to a waste canister whereby the aspiration means in the device unit automatically connects to an evacuation port on the waste canister such that there is a continuous aspiration path from the wound site/dressing to an exhaust port on the device.

Aptly, the exhaust port from the fluid path through the apparatus is provided with filter means to prevent offensive odours from being ejected into the atmosphere.

In general terms the device unit comprises an aspirant pump; means for monitoring pressure applied by the aspirant pump; a flowmeter to monitor fluid flow through the aspirant pump; a control system which controls the aspirant pump in response to signals from sensors such as the pressure monitoring means and the flowmeter, for example, and which control system also controls a power management system with regard to an on-board battery pack and the charging thereof and lastly a user interface system whereby various functions of the device such as pressure level set point, for example, may be adjusted (including stopping and starting of the apparatus) by a user. The device unit may contain all of the above features within a single unified casing.

In view of the fact that the device unit contains the majority of the intrinsic equipment cost therein ideally it will also be able to survive impact, tolerate cleaning in order to be reusable by other patients.

In terms of pressure capability the aspiration means may be able to apply a maximum pressure drop of at least −200 mmHg to a wound site/dressing. The apparatus is capable of maintaining a predetermined negative pressure even under conditions where there is a small leak of air into the system and a high exudate flow.

The pressure control system may prevent the minimum pressure achieved from exceeding for example −200 mmHg so as not to cause undue patient discomfort. The pressure required may be set by the user at a number of discreet levels such as −50, −75, −100, −125, −150, −175 mmHg, for example, depending upon the needs of the wound in question and the advice of a clinician. Thus suitable pressure ranges in use may be from −25 to −80 mmHg, or −50 to −76 mmHg, or −50 to −75 mmHg as examples. The control system may also advantageously be able to maintain the set pressure within a tolerance band of +/−10 mmHg of the set point for 95% of the time the apparatus is operating given that leakage and exudation rates are within expected or normal levels.

Aptly, the control system may trigger alarm means such as a flashing light, buzzer or any other suitable means when various abnormal conditions apply such as, for example: pressure outside set value by a large amount due to a gross leak of air into system; duty on the aspiration pump too high due to a relatively smaller leakage of air into the system; pressure differential between wound site and pump is too high due, for example, to a blockage or waste canister full.

The apparatus of the present invention may be provided with a carry case and suitable support means such as a shoulder strap or harness, for example. The carry case may be adapted to conform to the shape of the apparatus comprised in the joined together device and waste canister. In particular, the carry case may be provided with a bottom opening flap to permit the waste canister to be changed without complete removal of the apparatus form the carry case.

The carry case may be provided with an aperture covered by a displaceable flap to enable user access to a keypad for varying the therapy applied by the apparatus.

According to a second aspect of the present invention, there is provided apparatus that indicates status of at least one operating parameter associated with a topical negative pressure (TNP) system, comprising:
at least one LED that generates illumination, visible to a user of a TNP system, having at least one characteristic corresponding to a status of at least one operating parameter associated with the TNP system.

According to a third aspect of the present invention there is provided apparatus that indicates status of at least one operating parameter associated with a topical negative pressure (TNP) system; comprising:
at least one buzzer unit that generates at least one noise audible to a user having at least one characteristic corresponding to a status of at least one operating parameter associated with the TNP system.

Embodiments of the present invention provide a method and apparatus in which at least one operating parameter associated with a TNP system can be indicated to a user. A visible and/or audible cue such as a steady or flashing light or noise generated by a buzzer can be used so that the status can be used over a distance and possibly under poor light conditions. The audible or visible cue can be constant or repeated so as to provide further status information.

BRIEF DESCRIPTION OF THE DRAWINGS

In order that the present invention may be more fully understood, examples will now be described by way of illustration only with reference to the accompanying drawings, of which.

DETAILED DESCRIPTION OF SOME EXEMPLIFYING EMBODIMENTS

Figure 1:
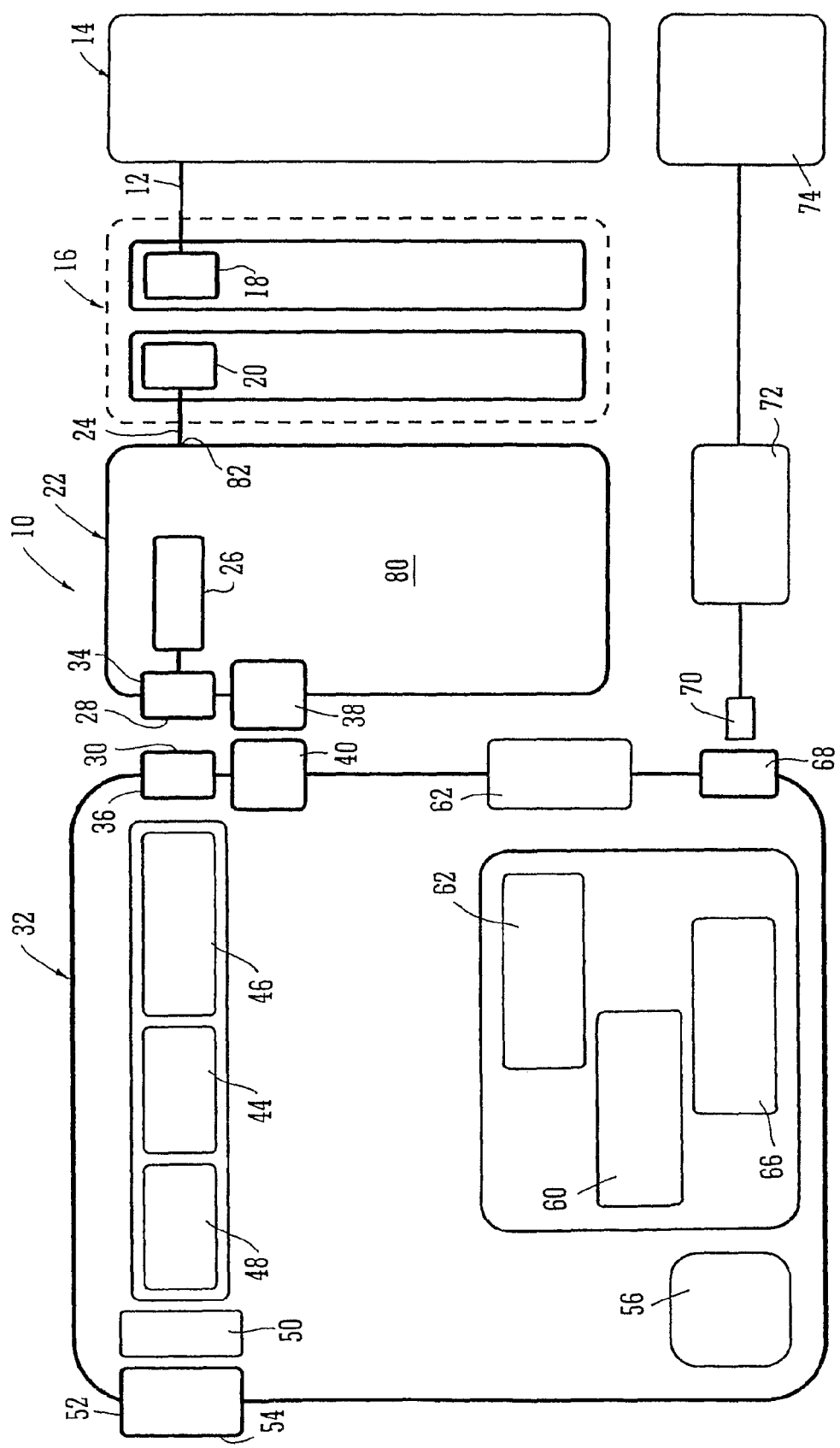
FIG. 1 shows a generalised schematic block diagram showing a general view of an apparatus and the constituent apparatus features thereof.

Referring now to FIGS. 1 to 4 of the drawings and where the same or similar features are denoted by common reference numerals.

FIG. 1 shows a generalised schematic view of an apparatus 10 of a portable topical negative pressure (TNP) system. It will be understood that embodiments of the present invention are generally applicable to use in such a TNP system. Briefly, negative pressure wound therapy assists in the closure and healing of many forms of "hard to heal" wounds by reducing tissue oedema; encouraging blood flow and granular tissue formation; removing excess exudate and may reduce bacterial load (and, therefore, infection). In addition the therapy allows for less disturbance of a wound leading to more rapid healing. The TNP system is detailed further hereinafter but in summary includes a portable body including a canister and a device with the device capable of providing an extended period of continuous therapy within at least a one year life span. The system is connected to a patient via a length of tubing with an end of the tubing operably secured to a wound dressing on the patient.

More particularly, as shown in FIG. 1, the apparatus comprises an aspiration conduit 12 operably and an outer surface thereof at one end sealingly attached to a dressing 14. The dressing 14 will not be further described here other than to say that it is formed in a known manner from well know materials to those skilled in the dressings art to create a sealed cavity over and around a wound to be treated by TNP therapy with the apparatus of the present invention. The aspiration conduit has an in-line connector 16 comprising connector portions 18, 20 intermediate its length between the dressing 14 and a waste canister 22. The aspiration conduit between the connector portion 20 and the canister 22 is denoted by a different reference numeral 24 although the fluid path through conduit portions 12 and 24 to the waste canister is continuous. The connector portions 18, 20 join conduit portions 12, 24 in a leak-free but disconnectable manner. The waste canister 22 is provided with filters 26 which prevent the escape via an exit port 28 of liquid and bacteria from the waste canister. The filters may comprise a 1 µm hydrophobic liquid filter and a 0.2 µm bacteria filter such that all liquid and bacteria is confined to an interior waste collecting volume of the waste canister 22. The exit port 28 of the waste canister 22 mates with an entry/suction port 30 of a device unit 32 by means of mutually sealing connector portions 34, 36 which engage and seal together automatically when the waste canister 22 is attached to the device unit 32, the waste canister 22 and device unit 32 being held together by catch assemblies 38, 40. The device unit 32 comprises an aspirant pump 44, an aspirant pressure monitor 46 and an aspirant flowmeter 48 operably connected together. The aspiration path takes the aspirated fluid which in the case of fluid on the exit side of exit port 28 is gaseous through a silencer system 50 and a final filter 52 having an activated charcoal matrix which ensures that no odours escape with the gas exhausted from the device 32 via an exhaust port 54. The filter 52 material also serves as noise reducing material to enhance the effect of the silencer system 50. The device 32 also contains a battery pack 56 to power the apparatus which battery pack also powers the control system 60 which controls a user interface system 62 controlled via a keypad (not shown) and the aspiration pump 44 via signals from sensors 46, 48. A power management system 66 is also provided which controls power from the battery pack 56, the recharging thereof and the power requirements of the aspirant pump 44 and other electrically operated components. An electrical connector 68 is provided to receive a power input jack 70 from a SELV power supply 72 connected to a mains supply 74 when the user of the apparatus or the apparatus itself is adjacent a convenient mains power socket.

Figure 2:
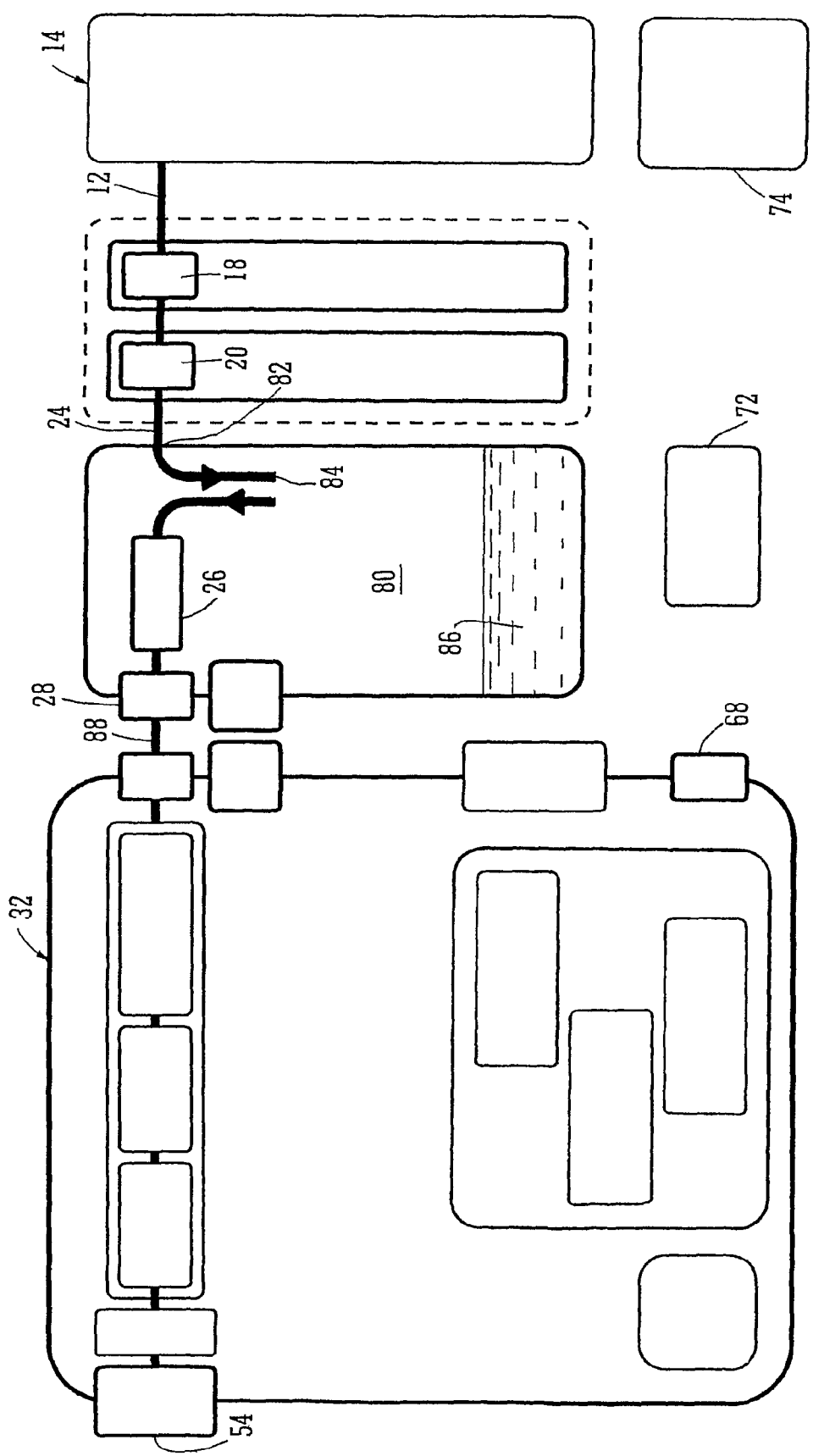
FIG. 2 shows a similar generalised schematic block diagram to FIG. 1 and showing fluid paths therein.

FIG. 2 shows a similar schematic representation to FIG. 1 but shows the fluid paths in more detail. The wound exudate is aspirated from the wound site/dressing 14 via the conduit 12, the two connector portions 18, 20 and the conduit 24 into the waste canister 22. The waste canister 22 comprises a relatively large volume 80 in the region of 500 ml into which exudate from the wound is drawn by the aspiration system at an entry port 82. The fluid 84 drawn into the canister volume 80 is a mixture of both air drawn into the dressing 14 via the semi-permeable adhesive sealing drape (not shown) and liquid 86 in the form of wound exudates. The volume 80 within the canister is also at a lowered pressure and the gaseous element 88 of the aspirated fluids is exhausted from the canister volume 80 via the filters 26 and the waste canister exhaust exit port 28 as bacteria-free gas. From the exit port 28 of the waste canister to the final exhaust port 54 the fluid is gaseous only.

Figure 3:
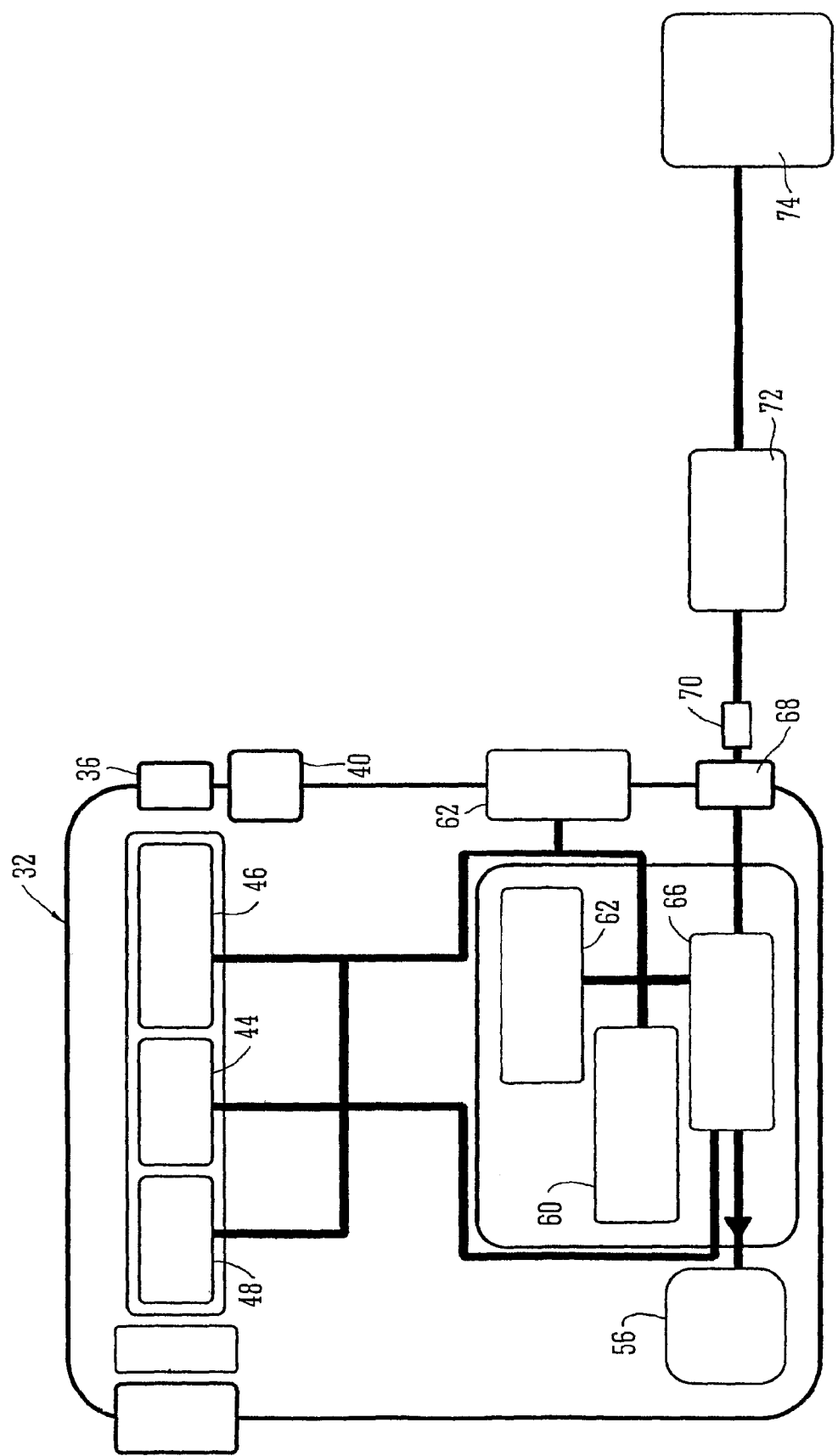
FIG. 3 shows a generalised schematic block diagram similar to FIG. 1 but of a device unit only and showing power paths for the various power consuming/producing features of the apparatus.

FIG. 3 shows a schematic diagram showing only the device portion of the apparatus and the power paths in the device of the apparatus embodying the present invention. Power is provided mainly by the battery pack 56 when the user is outside their home or workplace, for example, however, power may also be provided by an external mains 74 supplied charging unit 72 which when connected to the device 32 by the socket 68 is capable of both operating the device and recharging the battery pack 56 simultaneously. The power management system 66 is included so as to be able to control power of the TNP system. The TNP system is a rechargeable, battery powered system but is capable of being run directly from mains electricity as will be described hereinafter more fully with respect to the further figures. If disconnected from the mains the battery has enough stored charge for approximately 8 hours of use in normal conditions. It will be appreciated that batteries having other associated life times between recharge can be utilised. For example batteries providing less than 8 hours or greater than 8 hours can be used. When connected to the mains the device will run off the mains power and will simultaneously recharge the battery if depleted from portable use. The exact rate of battery recharge will depend on the load on the TNP system. For example, if the wound is very large or there is a significant leak, battery recharge will take longer than if the wound is small and well sealed.

Figure 4:
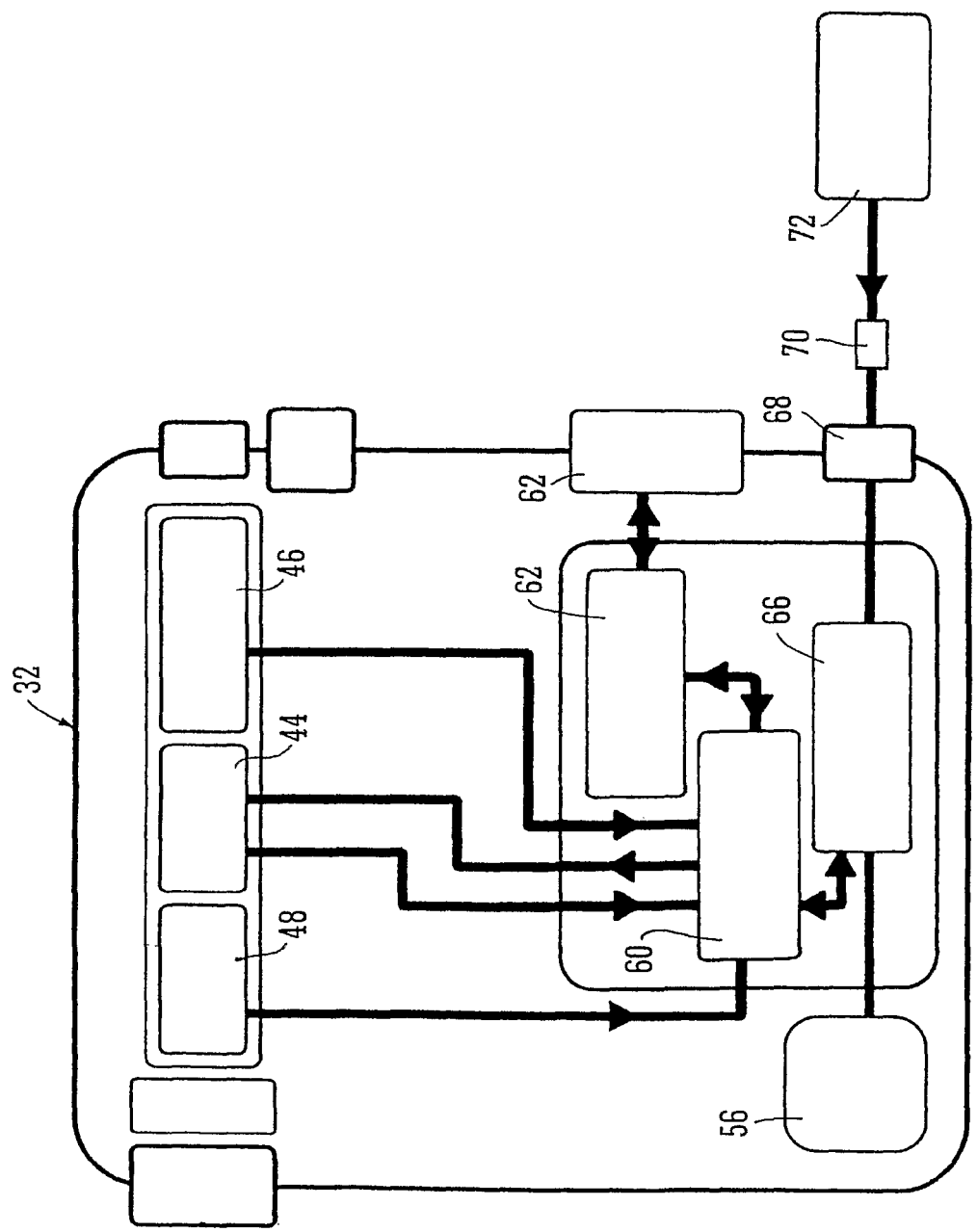
FIG. 4 shows a similar generalised schematic block diagram to FIG. 3 of the device unit and showing control system data paths for controlling the various functions and components of the apparatus.
Figure 5:
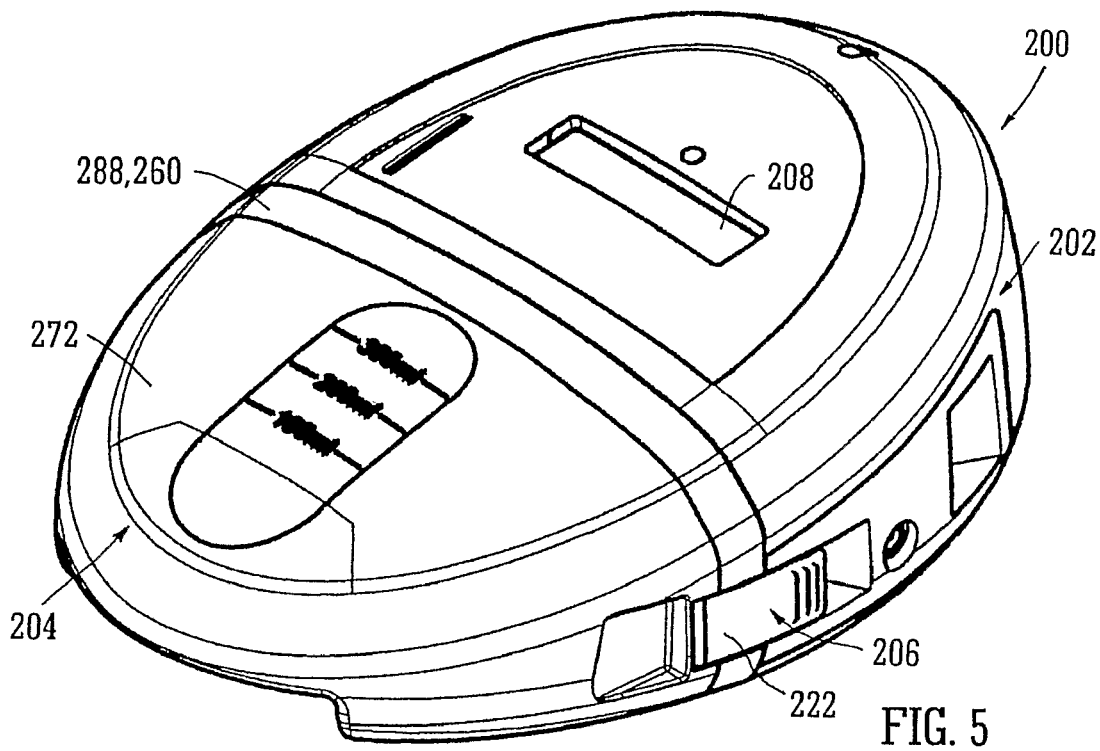
FIG. 5 shows a perspective view of an apparatus.
Figure 6:
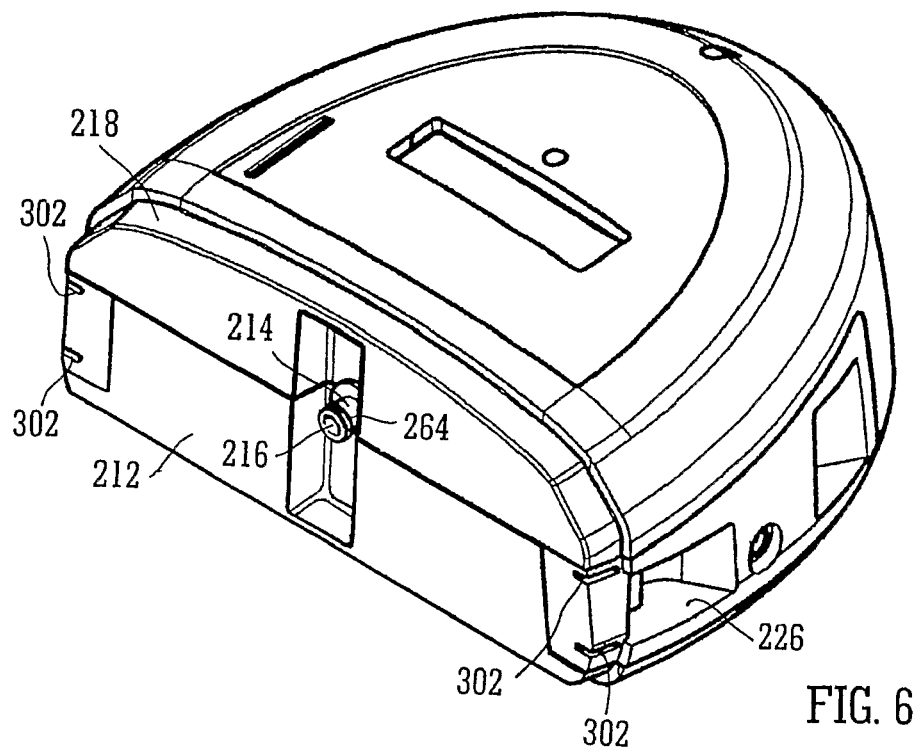
FIG. 6 shows a perspective view of an assembled device unit of the apparatus of FIG. 5.
Figure 7:
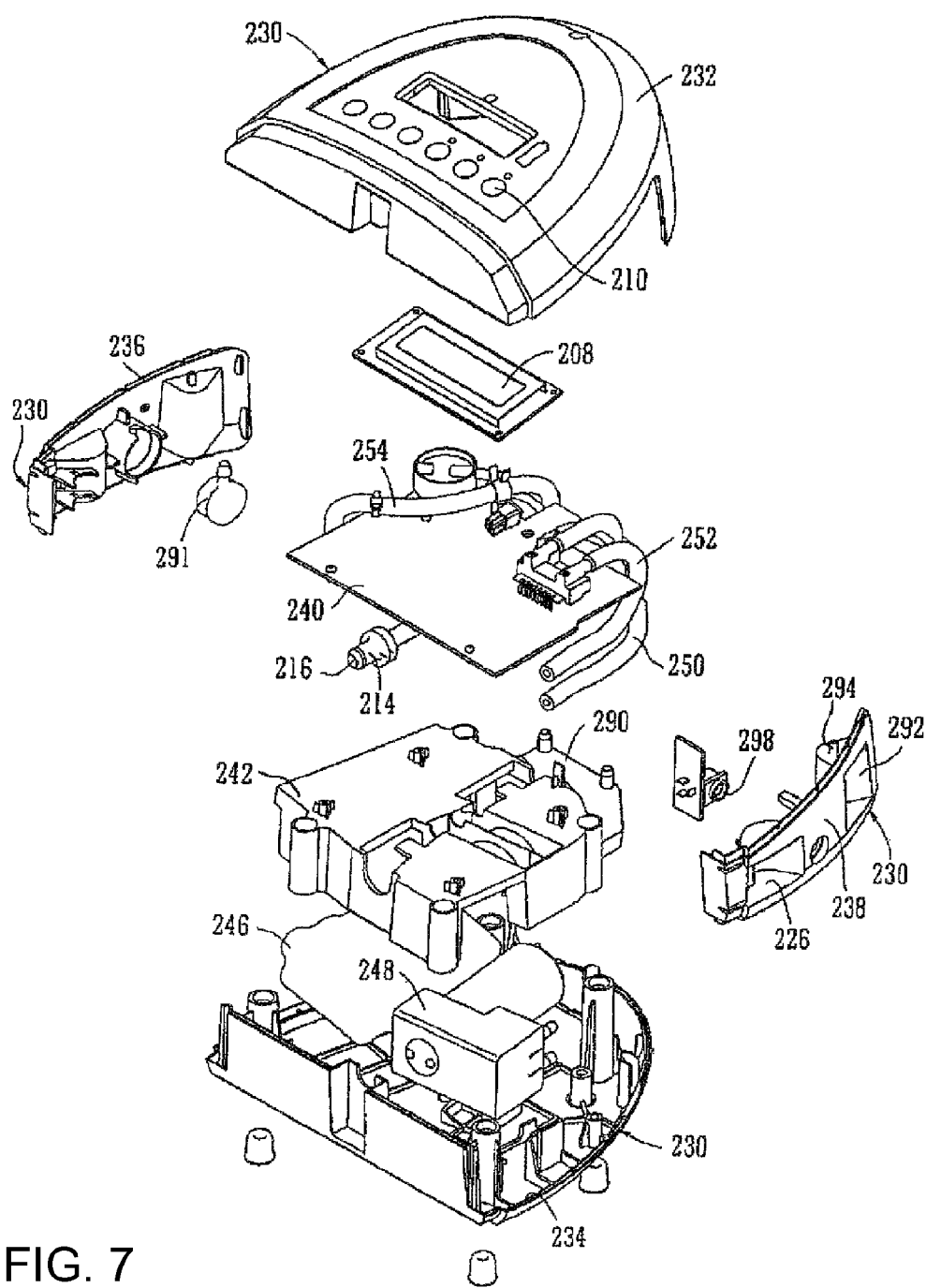
FIG. 7 shows an exploded view of the device unit of FIG. 6.

FIG. 4 shows the device 32 part of the apparatus embodying the present invention and the data paths employed in the control system for control of the aspirant pump and other features of the apparatus. A key purpose of the TNP system is to apply negative pressure wound therapy. This is accomplished via the pressure control system which includes the pump and a pump control system. The pump applies negative pressure; the pressure control system gives feedback on the pressure at the pump head to the control system; the pump control varies the pump speed based on the difference between the target pressure and the actual pressure at the pump head. In order to improve accuracy of pump speed and hence provide smoother and more accurate application of the negative pressure at a wound site, the pump is controlled by an auxiliary control system. The pump is from time to time allowed to "free-wheel" during its duty cycle by turning off the voltage applied to it. The spinning motor causes a "back electro-motive force" or BEMF to be generated. This BEMF can be monitored and can be used to provide an accurate measure of pump speed. The speed can thus be adjusted more accurately than can prior art pump systems.

According to embodiments of the present invention, actual pressure at a wound site is not measured but the difference between a measured pressure (at the pump) and the wound pressure is minimised by the use of large filters and large bore tubes wherever practical. If the pressure control measures that the pressure at the pump head is greater than a target pressure (closer to atmospheric pressure) for a period of time, the device sends an alarm and displays a message alerting the user to a potential problem such as a leak.

In addition to pressure control a separate flow control system can be provided. A flow meter may be positioned after the pump and is used to detect when a canister is full or the tube has become blocked. If the flow falls below a certain threshold, the device sounds an alarm and displays a message alerting a user to the potential blockage or full canister.

Figure 8:
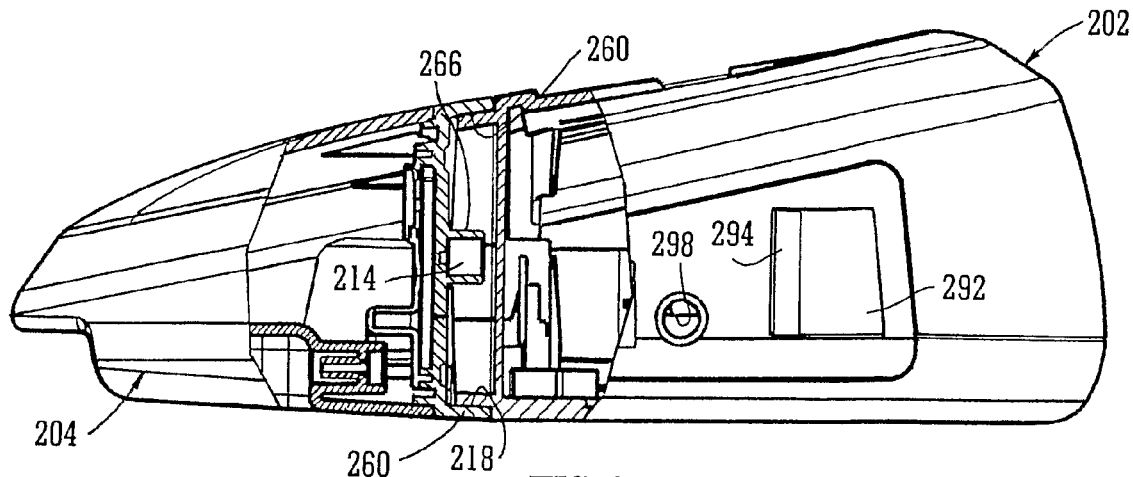
FIG. 8 shows a partially sectioned side elevation view through the interface between a waste canister and device unit of the apparatus.
Figure 9:
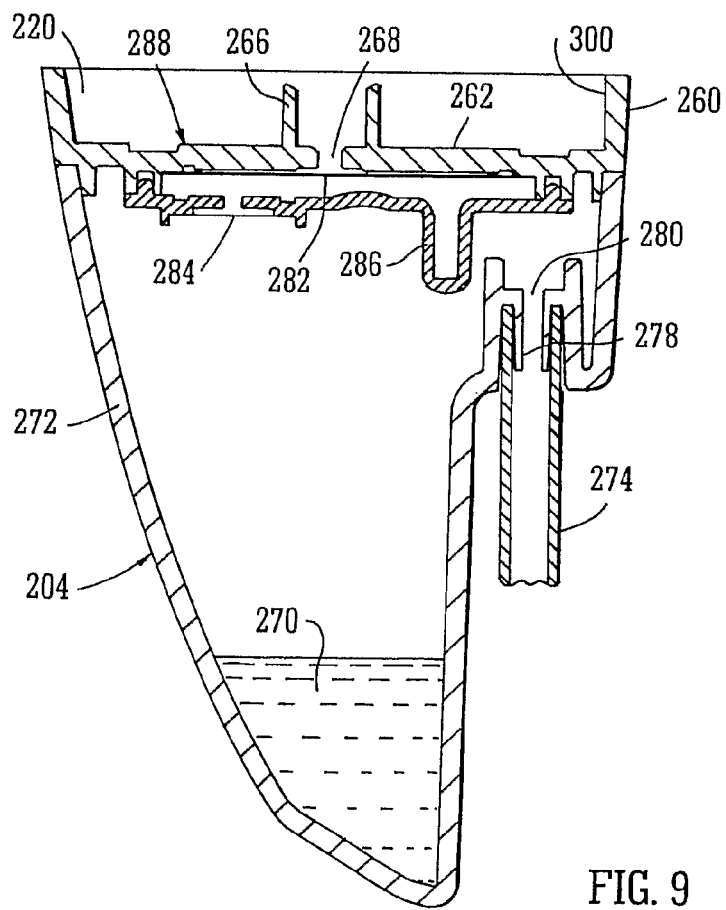
FIG. 9 shows a cross section through a waste canister of the apparatus of FIGS. 5 to 8.

Referring now to FIGS. 5 to 9 which show various views and cross sections of a preferred embodiment of apparatus 200 embodying the present invention. The preferred embodiment is of generally oval shape in plan and comprises a device unit 202 and a waste canister 204 connected together by catch arrangements 206. The device unit 202 has a liquid crystal display (LCD) 208, which gives text based feedback on the wound therapy being applied, and a membrane keypad 210, the LCD being visible through the membrane of the keypad to enable a user to adjust or set the therapy to be applied to the wound (not shown). The device has a lower, generally transverse face 212 in the centre of which is a spigot 214 which forms the suction/entry port 216 to which the aspiration means (to be described below) are connected within the device unit. The lower edge of the device unit is provided with a rebated peripheral male mating face 218 which engages with a co-operating peripheral female formation 220 on an upper edge of the waste canister 204 (see FIGS. 8 and 9). On each side of the device 202, clips 222 hinged to the canister 204 have an engaging finger (not shown) which co-operates with formations in recesses 226 in the body of the device unit. From FIG. 7 it may be seen that the casing 230 of the device unit is of largely "clamshell" construction comprising front and back mouldings 232, 234, respectively and left-hand and right-hand side inserts 236, 238. Inside the casing 230 is a central chassis 240 which is fastened to an internal moulded structural member 242 and which chassis acts as a mounting for the electrical circuitry and components and also retains the battery pack 246 and aspiration pump unit 248. Various tubing items 250, 252, 254 connect the pump unit 248 and suction/entry port 216 to a final gaseous exhaust via a filter 290. FIG. 8 shows a partially sectioned side elevation of the apparatus 200, the partial section being around the junction between the device unit 202 and the waste canister 204, a cross section of which is shown at FIG. 9. Theses views show the rebated edge 218 of the male formation on the device unit co-operating with the female portion 220 defined by an upstanding flange 260 around the top face 262 of the waste canister 204. When the waste canister is joined to the device unit, the spigot 214 which has an "O" ring seal 264 therearound sealingly engages with a cylindrical tube portion 266 formed around an exhaust/exit port 268 in the waste canister. The spigot 214 of the device is not rigidly fixed to the device casing but is allowed to "float" or move in its location features in the casing to permit the spigot 214 and seal 264 to move to form the best seal with the bore of the cylindrical tube portion 266 on connection of the waste canister to the device unit. The waste canister 204 in FIG. 9 is shown in an upright orientation much as it would be when worn by a user. Thus, any exudate 270 would be in the bottom of the internal volume of waste receptacle portion 272. An aspiration conduit 274 is permanently affixed to an entry port spigot 278 defining an entry port 280 to receive fluid aspirated from a wound (not shown) via the conduit 274. Filter members 282 comprising a 0.2 µm filter and 284 comprising a 1 µm filter are located by a filter retainer moulding 286 adjacent a top closure member or bulkhead 288 the filter members preventing any liquid or bacteria from being drawn out of the exhaust exit port 268 into the pump and aspiration path through to an exhaust and filter unit 290 which is connected to a casing outlet moulding at 291 via an exhaust tube (not shown) in casing side piece 236. The side pieces 236, 238 are provided with recesses 292 having support pins 294 therein to locate a carrying strap (not shown) for use by the patient. The side pieces 230 and canister 204 are also provided with features which prevent the canister and device from exhibiting a mutual "wobble" when connected together. Ribs (not shown) extending between the canister top closure member 288 and the inner face 300 of the upstanding flange 260 locate in grooves 302 in the device sidewalls when canister and device are connected. The casing 230 also houses all of the electrical equipment and control and power management features, the functioning of which was described briefly with respect to FIGS. 3 and 4 hereinabove. The side piece 238 is provided with a socket member 298 to receive a charging jack from an external mains powered battery charger (both not shown).

Figure 10:
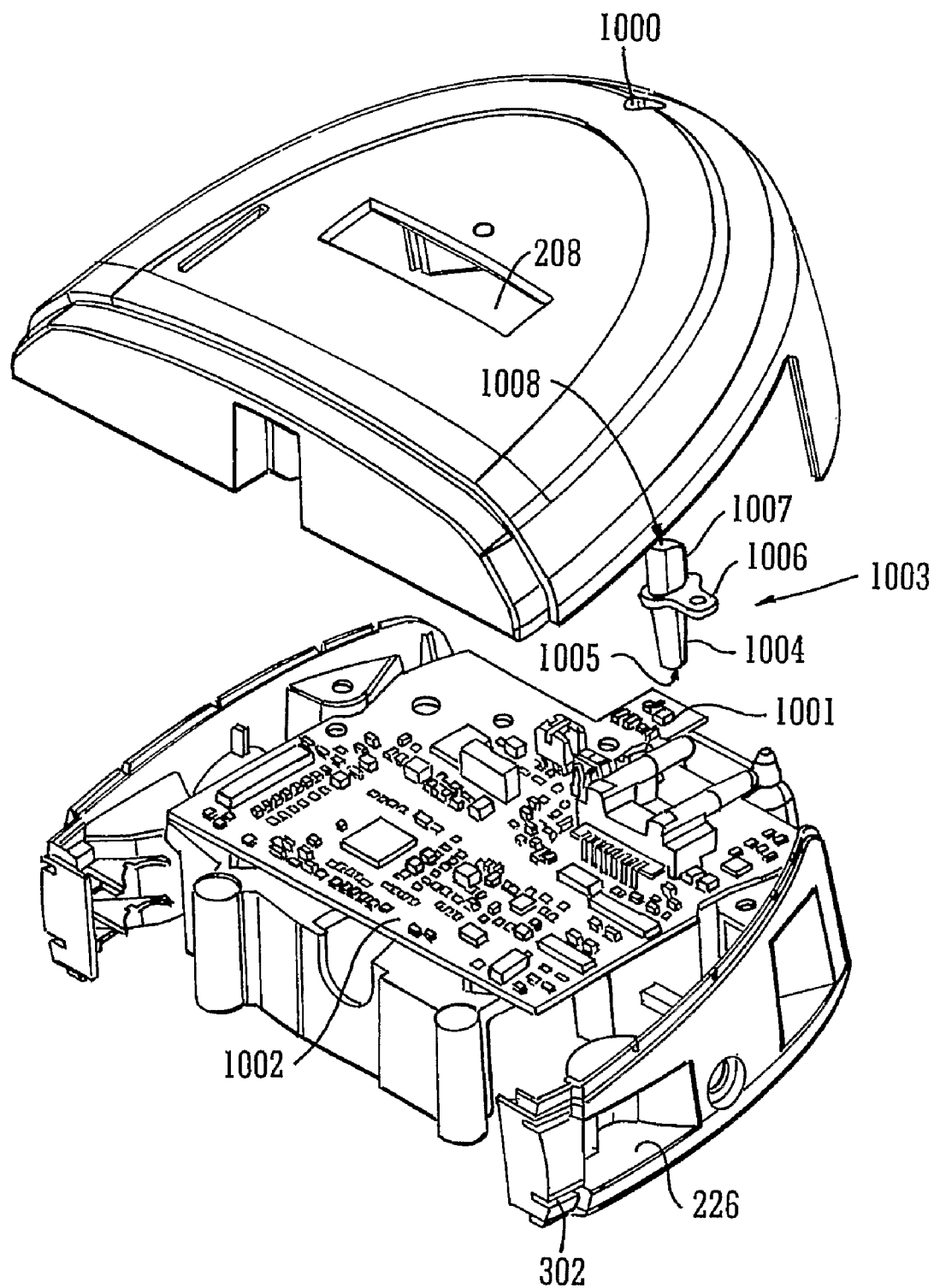
FIG. 10 shows an exploded view of a PCB and top case.

FIG. 10 illustrates how the status of one or more operating parameters associated with the TNP system can be indicated according to an embodiment of the present invention. It will be appreciated that the one or more operating parameters which may be indicated can be selected from a wide range of parameters associated with operation of the device. For example whether or not the device is operating and/or whether or not an onboard battery is running low and/or whether a medicament is being delivered and/or whether a negative pressure is being maintained with a predetermined threshold value and/or whether a pressure being delivered is dangerously outside normal operational characteristics. The status can be indicated by delivering a cue such as a visible cue using one or more windows 1000 formed in the casing of the device unit 202. One such window 1000 is illustrated in FIG. 10 but it will be appreciated that more windows could be provided so that the status of more than one operating parameter may be indicated simultaneously.

As illustrated in FIG. 10 which shows an exploded view of the device unit 202, an LED 1001 or other such illumination device such as an incandescent bulb is provided for each parameter which is to be indicated. Power and drive signals for the LED are provided on the PCB 1002.

A light guide 1003 is located at a position between the emission surface of the LED and the underside surface of the window 1000. The light guide 1003 includes a light receiving portion 1004 which includes a lower surface 1005 which is contoured to closely match the outer surface of the LED. In this way the lower portion 1004 of the light guide can be brought into intimate proximity with the LED. From the lower surface 1005 the lower portion 1004 of the light guide 1003 flares outwardly in a substantially thrusted conical fashion into a central fixing region 1006 which permits the light guide to be secured rigidly with respect to the casing. An upper portion 1007 of the light guide is substantially cylindrical and includes an upper light emitting surface 1008 which emits light through the window 1000 in a fashion to be highly visible to a user.

Figure 11:
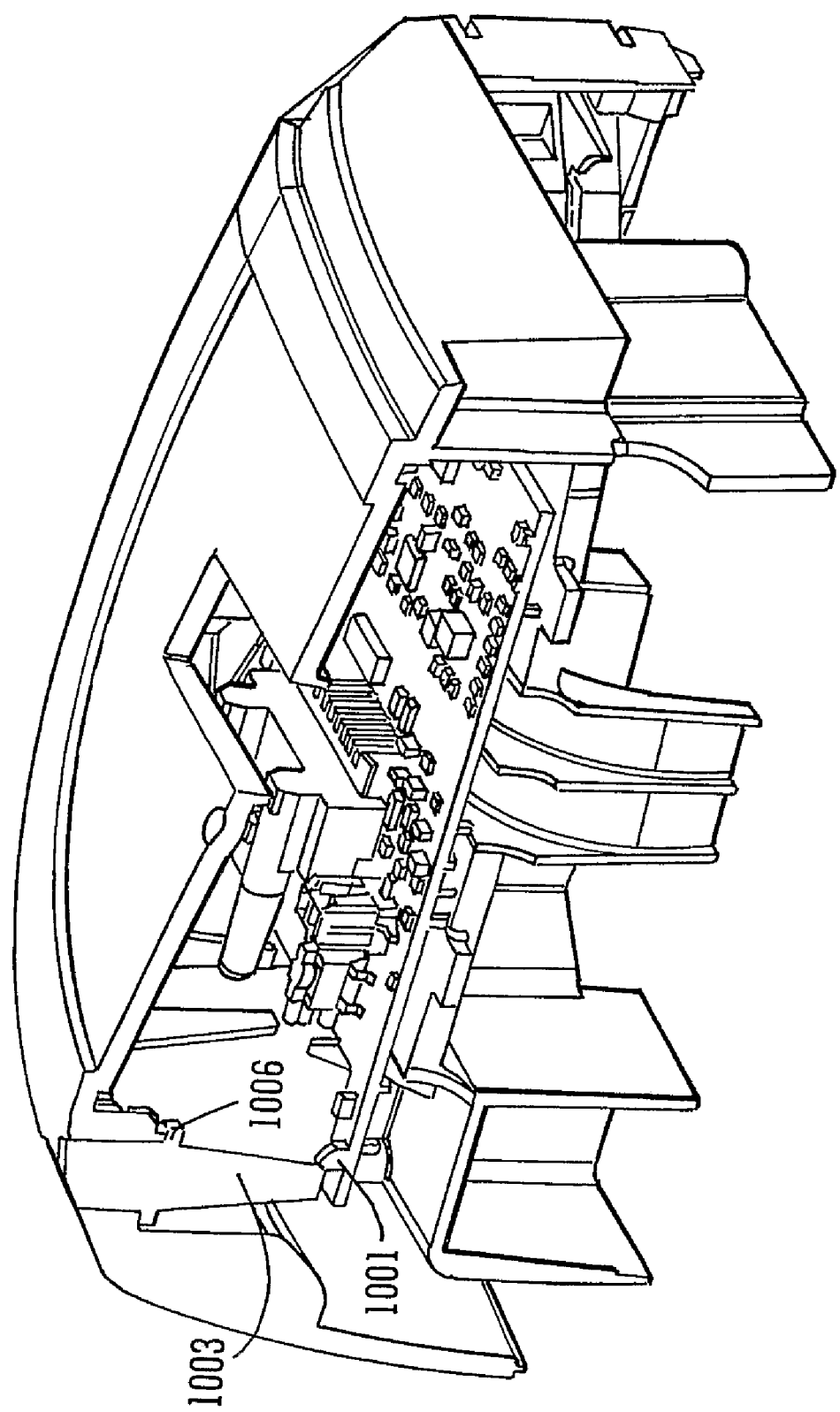
FIG. 11 shows a cross-section through a PCB and top case assembly.

FIG. 11 illustrates a cut away view of the device unit 202 showing the outer casing secured on the main body of the device unit with the light guide 1003 in position. The light guide 1003 acts as a light pipe ducting light from the PCB mounted LED to the prominent position on the device case work. Aptly the window and thus light emitted is visible from all major orientations so that a user is continually able to quickly check on the working parameters of the device.

Each LED has only three possible states. For example solid green, flashing green and solid red. Solid green indicates that topical negative pressure therapy is as expected. In other words that performance is adequate. Flashing green indicates that there are no urgent warnings and that therapy is still active. Examples of such use are when the battery is low or when the end of product life is expected. The flashing green light thus indicates to a user that whilst operating in an acceptable fashion at present there may be action required if therapy is to be continued. A solid red illumination indicates therapy failure. There may be a number of reasons for this such as leakage in the system or a blockage or a very low battery level. By providing three or optionally only two states for the LED a highly efficient system is provided whereby a user can rapidly verify status of parameters for the TNP system. In addition because of the low complexity the likelihood of interpretation error or reading occurring is minimised. It will be appreciated that this master status LED may be used in conjunction or as an alternative to the on screen text delivered through the LCD display 208 so that greater detailed feedback can be obtained if required.

Embodiments of the present invention thus provide the user or a carer with a system that gives simple, quick and accurate feedback to describe the TNP system state. Whilst current prior known devices have either no visual feedback on the therapy state for the user or user screen with hard to see text display or incorporate a confusing array of pressure figures and error messages embodiments of the present invention are not encumbered by such problems.

The use of an LED in a prominent position on the device that shows the state of the therapy being delivered with an easy to understand colour coding delivers a highly effective system. The user or carer can thus verify the status of the system very quickly without confusion of error codes or pressure figures.

Rather than delivering a visual cue such as illumination generated by an LED or other such light source an audible cue may alternatively or additionally be provided. A buzzer mounted on the circuit board is provided with control signals in the device and a sound tube directs sound to one or more holes (not shown) on the device case. Rather than a sound tube the speaker may be mounted close to the surface of the device casing. The pitch or length of time a sound is generated may indicate the status of an operating parameter. For example when a problem occurs during TNP operation a buzzer may sound. A single 'beep' may issue from time to time to indicate that a battery level is getting low.

It will be appreciated that according to embodiments of the present invention the LCD display 208 may be omitted from the device unit with only one or a few illumination or sound windows 1000 being provided to indicate proper function. With such a system, because it is not icon based and would give audible and/or visual feedback based purely on the tone, repetitiveness and/or colour of the LED, a simple to use system is provided. In addition illumination or sound is not language specific which makes the device unit applicable for multi-regional use or use by users of differing nationality and ability.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

What is claimed is:

1. A method of indicating status of at least one operating parameter associated with a topical negative pressure (TNP) system, comprising the steps of:
    generating a visual indicator as an illumination from an LED, the visual indicator having at least three characteristics corresponding to a status of at least one operating parameter associated with the TNP system, the at least three characteristics comprising:
        a first characteristic comprising a first solid color for indicating a first status;
        a second characteristic comprising a second solid color for indicating a second status, the second solid color different from the first solid color; and
        a third characteristic comprising a flashing of the first color for indicating a third status,
    wherein the indicated status comprises at least one of a normal operation, a failed operation and a non-urgent warning, and
    wherein generating the visual indicator comprises generating the illumination from the LED located in a cavity region of a case of the TNP system via a light-pipe element directing the illumination to a viewing window element visible to a user on an outer surface of the case, the viewing window element comprising a prismed surface.

2. The method as claimed in claim 1, further comprising the steps of:
    generating the illumination from the LED mounted at a visible surface of the case of the TNP system.

3. The method as claimed in claim 1, further comprising the steps of:
    providing illumination having only two possible colors from the LED.

4. The method as claimed claim 1, further comprising the steps of:
    providing illumination having only a solid or flashing state from the LED.

5. The method as claimed in claim 1, further comprising the steps of:
    via an illuminated user display located on an outer surface of a case of the TNP system, providing light or graphic symbols indicating further status information associated with operation of the TNP system.

6. The method as claimed in claim 1, further comprising the steps of:
    generating an audible noise from a buzzer unit corresponding to the status of at least one operating parameter associated with the TNP system.

7. An apparatus that indicates status of at least one operating parameter associated with a topical negative pressure (TNP) system, comprising:
    an LED that generates an illumination visible to a user of a TNP system, the illumination having at least three characteristics corresponding to a status of at least one operating parameter associated with the TNP system, the at least three characteristics comprising:
        a first characteristic comprising a first solid color for indicating a first status;
        a second characteristic comprising a second solid color for indicating a second status, the second solid color different from the first solid color; and
        a third characteristic comprising a flashing of the first color for indicating a third status,
    wherein the indicated status comprises at least one of a normal operation, a failed operation and a non-urgent warning,
    wherein the TNP system comprises:
        a source of negative pressure configured to provide negative pressure to a wound dressing through a fluid flow path,
        a case configured to enclose the source of negative pressure, and
        a collection canister configured to be attached to the case, the collection canister configured to be placed in the fluid flow path between the source of negative pressure and the dressing,
        a viewing window element disposed at a visible surface of the case, and
        a light-pipe element configured to direct the illumination generated by the LED to the viewing window, and
    wherein:
        the LED is mounted in a cavity region in the case, and
        the viewing window element comprises a prismed surface.

8. The apparatus as claimed in claim 7, wherein the LED is mounted at a visible surface of the case of the TNP system.

9. The apparatus as claimed in claim 7, wherein
    the light-pipe element comprises a body formed from an at least partially transparent material, said body comprising a generally conical portion with a narrow end locatable proximate to the LED and a remainder end extending into a substantially cylindrical portion.

10. The apparatus as claimed in claim 9, wherein the narrow end of the body of the light-pipe element has at least one recessed end region to closely fit over a respective LED.

11. The apparatus as claimed in claim 9, further comprising:
    a circular outer surface of the cylindrical portion of the light-pipe element body provides the viewing window.

12. The apparatus as claimed in claim 7, further comprising:
at least one buzzer unit that generates at least one noise audible to a user having at least one characteristic corresponding to the status of at least one operating parameter associated with the TNP system.

13. The method according claim 1 wherein the at least one operating parameter comprises at least one of power, operating efficiency, battery life, number of doses left, and therapy status.

14. The apparatus according claim 7 wherein the at least one operating parameter comprises at least one of power, operating efficiency, battery life, number of doses left, and therapy status.

15. A method for indicating a status of at least one operating parameter associated with a topical negative pressure (TNP) system comprising:
generating a visual indicator as an illumination from an LED, the visual indicator having at least two characteristics corresponding to a status of at least one operating parameter associated with the TNP system, the at least two characteristics comprising:
  a first characteristic for indicating a first status comprising a first solid color; and
  a second characteristic for indicating a second status comprising at least one of a second solid color different from the first solid color and a flashing of the first color,
wherein the indicated status comprises at least one of a normal operation, a failed operation and a non-urgent warning,
wherein generating the visual indicator comprises generating the illumination from the LED located in a cavity region of a case of the TNP system via a light-pipe element directing the illumination to a viewing window visible to a user, the viewing window comprising a prismed surface.

16. The method of claim 1, wherein the at least one operating parameter comprises therapy status and battery capacity and generating the visual indicator comprises generating the illumination corresponding to therapy status and battery capacity from a single LED.

17. The apparatus of claim 7, wherein the at least one operating parameter comprises therapy status and battery capacity and the apparatus comprises a single LED configured to generate the illumination corresponding to therapy status and battery capacity.

18. The method of claim 15, wherein the at least one operating parameter comprises therapy status and battery capacity and generating the visual indicator comprises generating the illumination corresponding to therapy status and battery capacity from a single LED.

* * * * *